(12) United States Patent
Harrison et al.

(10) Patent No.: US 7,896,001 B2
(45) Date of Patent: Mar. 1, 2011

(54) PRESSURE-RESPONSIVE DEVICE AND ASSOCIATED METHOD OF MANUFACTURE

(75) Inventors: Nigel Harrison, Cambridgeshire (GB); Daniel Godfrey, Cambridgeshire (GB)

(73) Assignee: Pfizer Limited, Sandwich, Kent (GB)

( * ) Notice: Subject to any disclaimer, the term of this patent is extended or adjusted under 35 U.S.C. 154(b) by 0 days.

(21) Appl. No.: 10/398,067

(22) PCT Filed: Sep. 24, 2001

(86) PCT No.: PCT/GB01/04241

§ 371 (c)(1), (2), (4) Date: Aug. 28, 2003

(87) PCT Pub. No.: WO02/26300

PCT Pub. Date: Apr. 4, 2002

(65) Prior Publication Data

US 2004/0107962 A1    Jun. 10, 2004

(30) Foreign Application Priority Data

Sep. 29, 2000 (GB) ................................ 0023845.1
Nov. 22, 2000 (GB) ................................ 0028444.8

(51) Int. Cl.
| | |
|---|---|
| A61M 11/00 | (2006.01) |
| A61M 15/00 | (2006.01) |
| F16K 31/02 | (2006.01) |
| A23P 1/00 | (2006.01) |
| F16F 1/18 | (2006.01) |
| H01H 1/10 | (2006.01) |
| B28B 5/00 | (2006.01) |
| B28B 11/08 | (2006.01) |
| B27N 3/10 | (2006.01) |
| B29C 45/14 | (2006.01) |
| B29B 7/00 | (2006.01) |

(52) U.S. Cl. ........................ 128/200.14; 128/200.23; 128/203.12; 128/204.23; 425/542; 267/160; 267/163; 200/512; 264/251; 264/257; 264/259; 264/271.1; 264/288.4; 264/291; 264/328.1; 264/275; 264/279; 264/328.9

(58) Field of Classification Search ................. 425/542; 128/200.14, 200.23, 203.12, 204.23; 267/160, 267/163; 200/512; 264/251, 257, 259, 271.1, 264/288.4, 291, 328.1, 275, 279, 328.9
See application file for complete search history.

(56) References Cited

U.S. PATENT DOCUMENTS 2,715,418 A * 8/1955 Van Derbeck ............... 137/510
3,590,694 A * 7/1971 Prescott et al. ................. 92/20
4,218,959 A * 8/1980 Numaguchi et al. ..... 92/103 SD (Continued)

FOREIGN PATENT DOCUMENTS

EP    0558787 A1    8/1993

(Continued)

Primary Examiner—Patricia M Bianco
Assistant Examiner—Nihir Patel
(74) Attorney, Agent, or Firm—Reising Ethington P.C.

(57) ABSTRACT

There is provided a pressure-responsive device (40) suitable for use in an inhaler, the pressure-responsive device (40) comprising a closed frame (42) over which is fixed a membrane (44), a tongue (46) being supported on the membrane (44). Two upstanding wings (50) are integrally moulded with the tongue (46) and incorporate square apertures (52). A method of manufacturing the pressure-responsive device (40) is also provided.

8 Claims, 10 Drawing Sheets

U.S. PATENT DOCUMENTS

| | | |
|---|---|---|
| 5,027,808 A | 7/1991 | Rich et al. |
| 5,718,327 A * | 2/1998 | Wu .............................. 200/344 |
| 6,026,808 A * | 2/2000 | Armer et al. ........... 128/200.23 |
| 6,341,603 B1 * | 1/2002 | Howlett ................. 128/200.23 |
| 6,821,467 B2 * | 11/2004 | Wolfe et al. .................. 264/155 |

FOREIGN PATENT DOCUMENTS

WO   WO 98/52634   * 11/1998

* cited by examiner

PRESSURE-RESPONSIVE DEVICE AND ASSOCIATED METHOD OF MANUFACTURE

FIELD OF THE INVENTION

This invention relates to pressure-responsive devices suitable for use in an inhaler which dispenses medication, an inhaler incorporating such a pressure-responsive device and an associated method of manufacture.

BACKGROUND TO THE INVENTION

Pressure-responsive devices, such as those comprising diaphragms, are well known. However where these pressure-responsive elements are intended to deflect in response to pressure differentials resulting from inhalation of air, then they are often unsatisfactory as they require relatively large pressure differentials for deflection to occur. A person whose inhalation of breath is intended to provide this pressure differential can have difficulty in producing sufficient force to deflect the pressure-responsive element. This is particularly so in asthma inhalers used to dispense doses of medication in response to inhalation by a patient, rather than in response to a manual trigger.

It is an aim of the present invention to provide a pressure-responsive device which is sensitive to small pressure differentials, an inhaler incorporating such a pressure-responsive device and also an associated method of manufacture.

The invention is not intended to be limited to use only in the field of inhalers, but may be applicable in any field requiring a pressure-responsive device sensitive to small pressure differentials.

SUMMARY OF THE INVENTION

In accordance with one aspect of the present invention, there is provided a pressure-responsive device comprising a support bearing a flexible sheet, wherein the flexible sheet carries a tongue moveable in response to changes in pressure.

The pressure-responsive device is particularly of use within breath-operated inhalers used for dispensing medication, where movement of the tongue can be used to trigger dispensing of a dose, but is generally applicable to any field requiring a pressure-responsive device sensitive to small pressure differentials.

The support is preferably a closed frame, such as a rectangular frame, with an entire peripheral edge of the flexible sheet fixed to the frame. The sheet is thus sealed to the frame. The support can be of any configuration, and thus can be oval in shape, or if appropriate, an open frame such as a U-shaped frame.

Thus the flexible sheet may be provided by a membrane further comprising a slack region, the slack region thus providing an area over which the membrane is deflectable within the frame.

The tongue preferably extends across the membrane such that an upper part of the tongue is carried by the slack region of the membrane. In such an arrangement, the upper part of the tongue deflects in response to differences in air pressure due to travel permitted by the slack region of the membrane, and the remainder of the membrane acts as a hinging means about which the upper part of the tongue pivots. There is thus no connection between the tongue and the frame, the tongue solely being carried by the membrane. The tongue is thus independently movable of the frame.

The tongue may be tapered along its length, having an upper broad region and a lower narrow region, with the upper region being carried by the slack region of the membrane.

The tongue may further comprise two wings attached to one face of the tongue, the two wings each having an aperture for receiving part of a trigger mechanism. When the pressure-responsive device is used within a breath-operated inhaler, movement of the tongue causes triggering of the trigger mechanism due to part of the trigger mechanism being received within the wing apertures.

Typically the end of the tongue furthest from the hinging means deflects approximately 4 mm about the hinging means, i.e. a total deflection of 8 mm and there may be a degree of translation of the end of the tongue closest to the hinging means as a result of the tongue being carried on the membrane. Thus a translation of the hinging means within the frame may occur, this translation being of a much lesser degree than the end of the tongue furthest from the hinging means, and typically being around 0.5 mm.

The frame and tongue are preferably made from plastics material, such as polyethylene or high density polyethylene, and are substantially rigid. Typically the frame has dimensions of around 60 mm×25 mm with a thickness of around 4 mm, with the tongue sitting on the membrane within the frame, and there being a clearance region around the tongue such that the tongue and frame are separated and do not interconnect at any point.

The membrane is preferably made of a thin flexible web of plastics material, the web having a thickness of around 10 microns. Typically the web is made of high density polyethylene which is generally inelastic. Alternatively EBA (ethylene butyl acrylate) and EMA (ethylene methyl acrylate) films may be used.

The membrane may be fixed to the frame as a result of an injection moulding process used to make the pressure-responsive device.

Typically in use the pressure-responsive device is used to seal an air passageway within a breath-operated inhaler, with inhalation by a patient and the associated pressure drop causing deflection of the tongue. The movement of the tongue can be used to trigger mechanisms outside the passageway so as to result in dispensing of a dose.

Thus in accordance with another aspect of the invention there is provided a dosing device, or inhaler, for dispensing a dose material comprising a body comprising an air passageway, a trigger mechanism and a pressure-responsive device as aforesaid comprising a support, a flexible sheet and a tongue, wherein the pressure-responsive device is placed in sealing engagement with an end of the air passageway within the body so as to seal the trigger mechanism therefrom, and the trigger mechanism is actuated by movement of the tongue in response to pressure differential within the air passageway. When a patient requires medication, they place their mouth over one end of the air passageway so as to create a substantially air-tight seal, and inhale. This creates a pressure drop within the passageway. The tongue deflects in response to this change in pressure and so triggers the trigger mechanism to dispense a dose.

The trigger mechanism is preferably attached to the tongue so that movement of the tongue directly actuates the trigger mechanism without the need for intervening linkages. Connecting the trigger mechanism to the tongue also ensures that the tongue is held in a relatively fixed position, ready for deflection on inhalation.

The pressure-responsive device may desirably form a snapfit connection with the end of the air passageway within the body so that sealing engagement between the pressure-responsive device and the air passageway is readily achieved.

In accordance with a yet further aspect of the present invention, there is provided a method of making a pressure-responsive device as aforesaid, comprising placing a sheet of material between upper and lower injection moulding tools, closing the tools together, injection moulding a support and a tongue within the tools and providing a slack region in the sheet between the support and the tongue.

The support and the tongue may either be formed on the same side of the sheet, or alternatively on opposite sides.

The method may further comprise distorting the sheet by stretching to achieve plastic deformation of a region of the sheet, so as to provide the slack region.

Alternatively the method may further comprise drawing part of the sheet into the tool as forming occurs, thereby to limit the amount of stretch undergone by the sheet. This has the advantage of producing a stretched sheet which is less likely to perforate during manufacture of the pressure-responsive device.

BRIEF DESCRIPTION OF THE DRAWINGS

The invention will now be described, by way of example, and with reference to the accompanying drawings in which.

DETAILED DESCRIPTION OF THE PREFERRED EMBODIMENTS

Figure 1:
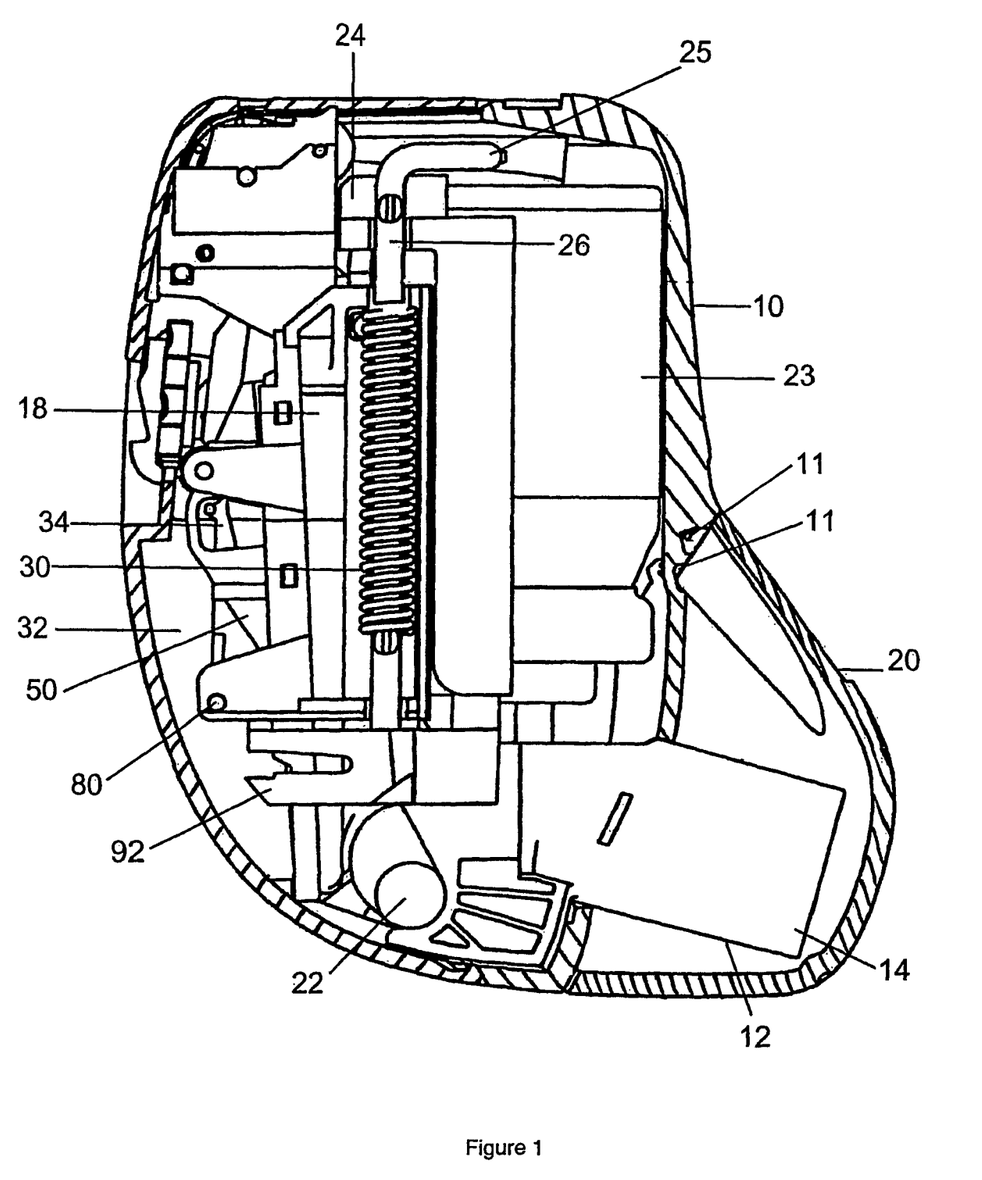
FIG. 1 shows a cut-away view of an inhaler incorporating a pressure-responsive device in accordance with the present invention.
Figure 2:
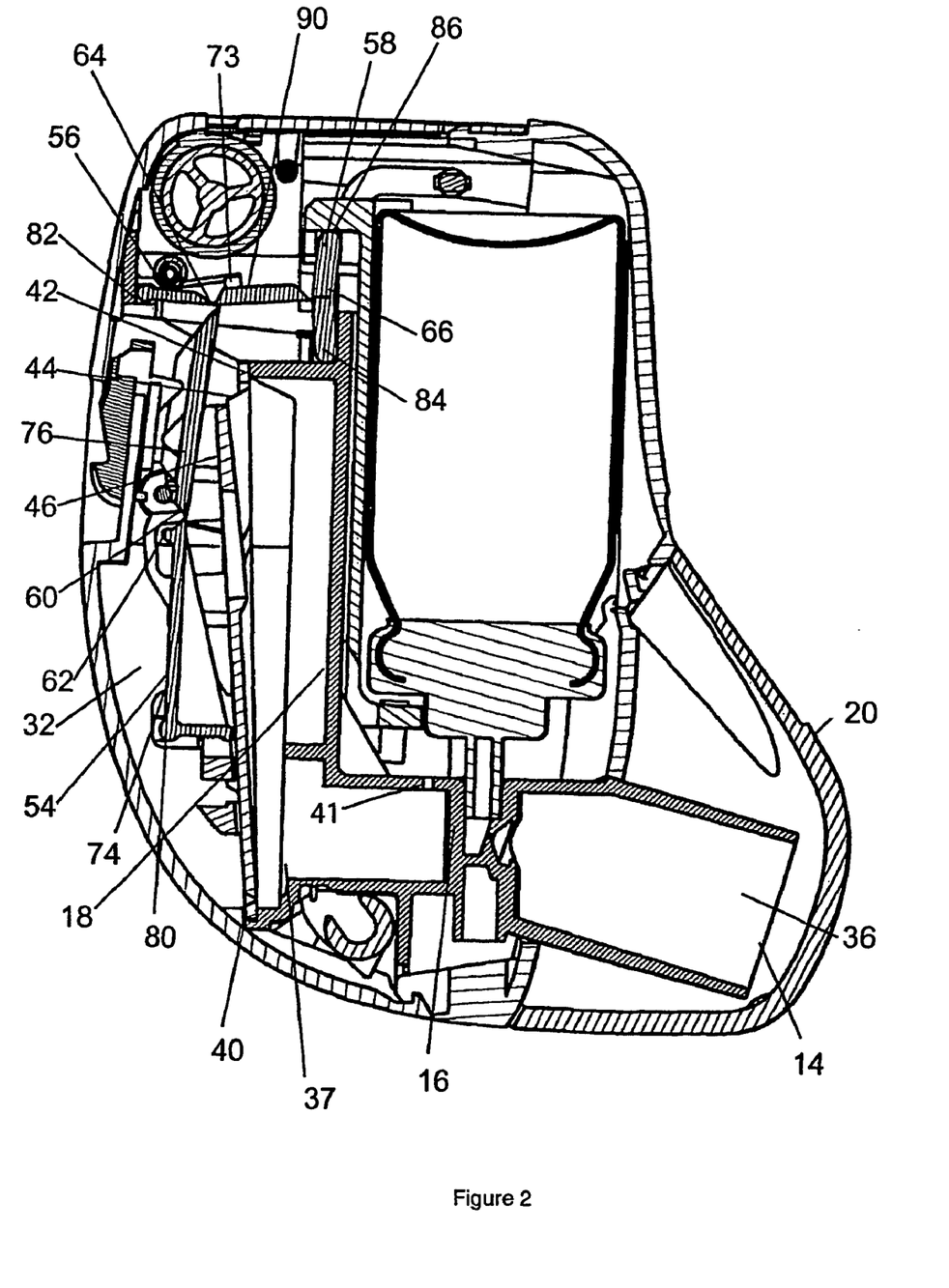
FIG. 2 shows a vertical section through the inhaler, showing the inhaler in a pre-firing state.
Figure 3:
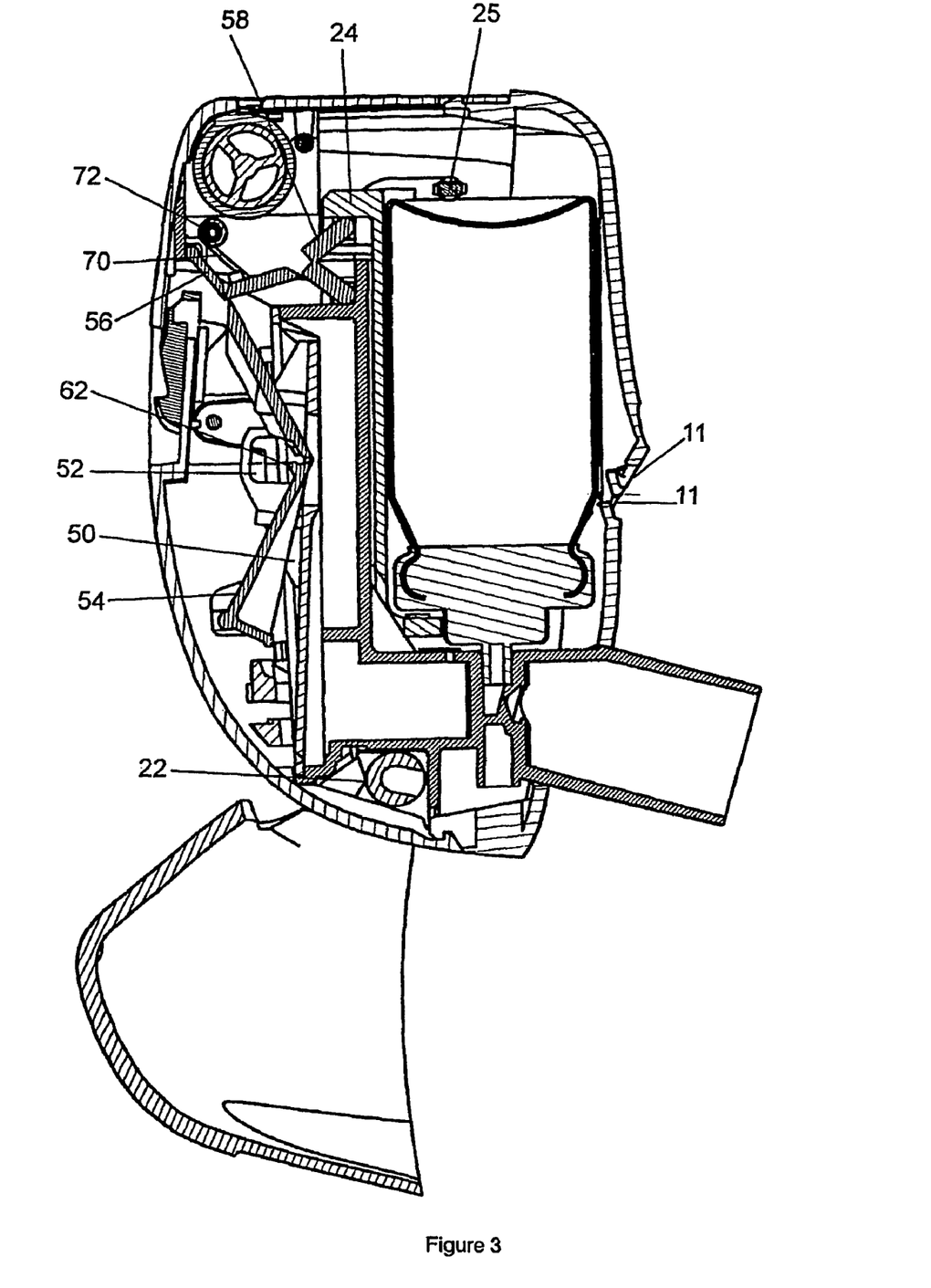
FIG. 3 shows a vertical section through the inhaler, showing the inhaler in a post-firing state.

FIGS. 1, 2 and 3 show a breath-operated metered dose inhaler (MDI) incorporating a pressure-responsive device in accordance with the present invention. The MDI comprises a hollow outer body 10 typically made of plastics material, which includes apertures 11, and a mouthpiece moulding 12 comprising a mouthpiece 14, stem block 16 and chassis 18. A cover 20 for the mouthpiece is attached to the body by a cam 22 which pivots as the cover 20 is moved. The inhaler is shown in FIGS. 1 and 2 in a rest position awaiting firing to deliver a dose of medication from a canister 23 contained within body 10. The medication is suspended in a propellant of the hydrofluoroalkane type (HFA's).

The canister 23 is positioned within the body 10 between a canister carriage 24 and a steel bar or hook 25 forming part of a substantially u-shaped spring carriage 26 bearing two main springs 30 disposed on either side of the canister 23. In this rest position of the inhaler, the canister is relatively loose and is only held in place because a valve stem of the canister is held within a stem block 16.

The body 10 defines a holding area 32 in which a dose-actuation mechanism 34 is situated and also a conduit forming an air passage 36, at an inner end of which pressure-responsive device 40 is located in sealing engagement. The air passage is in fluid communication with apertures 11 via two small apertures 41, see FIG. 2, in the wall of the conduit. The pressure-responsive device 40 comprises a closed frame 42 over which is fixed a plastics membrane 44, with a tongue 46 being supported on the membrane, and two upstanding wings 50 integrally moulded with the tongue and incorporating square apertures 52. The pressure-responsive device 40 is discussed in more detail with reference to FIGS. 6 to 9.

Figure 4:
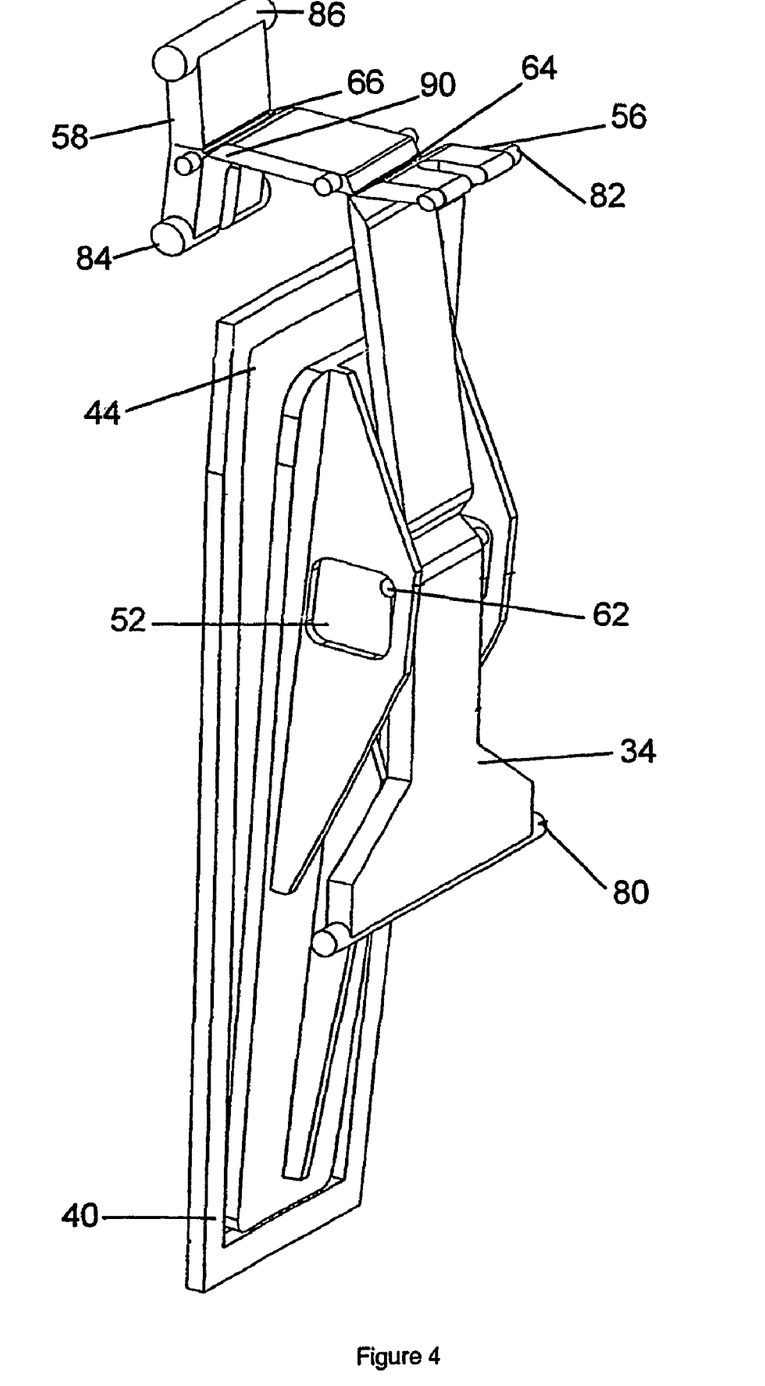
FIG. 4 shows a detailed perspective view of the pressure-responsive device and the trigger mechanism, before firing of a dose.

The trigger mechanism 34 comprises a trigger link 54, an intermediate link 56 and a power link 58 and is typically made as a one-piece moulding from polypropylene. The trigger link 54 is around 30 mm in length, 7 mm wide, 1 mm thick and tapers to around 100 microns thick at its hinging point 60. Pins 62 are moulded into the link near the hinging point and sit within the square apertures of wings 50. The intermediate link 56 is around 1 mm thick, tapering to 200 microns thick at its hinging point 64, and the power link 58 is around 2 mm thick, tapering to around 0.5 mm thick at its hinging point 66. A biasing torsion spring 70 is held on a roll pin 72 supported in the chassis 18, the biasing torsion spring 70 being held in compression by the trigger link 54 between the chassis 18 and a mounting position 73 on the uppermost surface of the intermediate link 56.

In FIGS. 1, 2 and 4, the triggering mechanism 34 is in the rest position and the device is ready to dispense a dose. The trigger link 54 is held in a stable over center position as a result of biasing torsion spring 70, and each pin 62 rests against one edge of the respective square aperture 52. The trigger link is in a substantially vertical configuration, with a first element 74 and a second element 76 subtending nearly 180° of arc. The near vertical trigger link 54 holds the intermediate link 56 and power link 58 at unstable under center positions.

Pin joints 80, 82, 84, 86 secure the loose ends of the mechanism within the body. The end of the second element 76 furthest from the hinging point 62 is permanently hinged to the intermediate link 56 close to the hinge 64, with end 90 of the intermediate link hinged to the power link close to the hinging point 66 of the power link. A leg of the biasing torsion spring 70 sits in a saddle 73 on the intermediate link close to the hinge 64 of the intermediate link and allows the intermediate link 56 to be substantially straight, although slightly under center.

The elements forming the trigger mechanism and the pressure-responsive device are shown in detail in FIG. 4, before firing of a dose.

Figure 5:
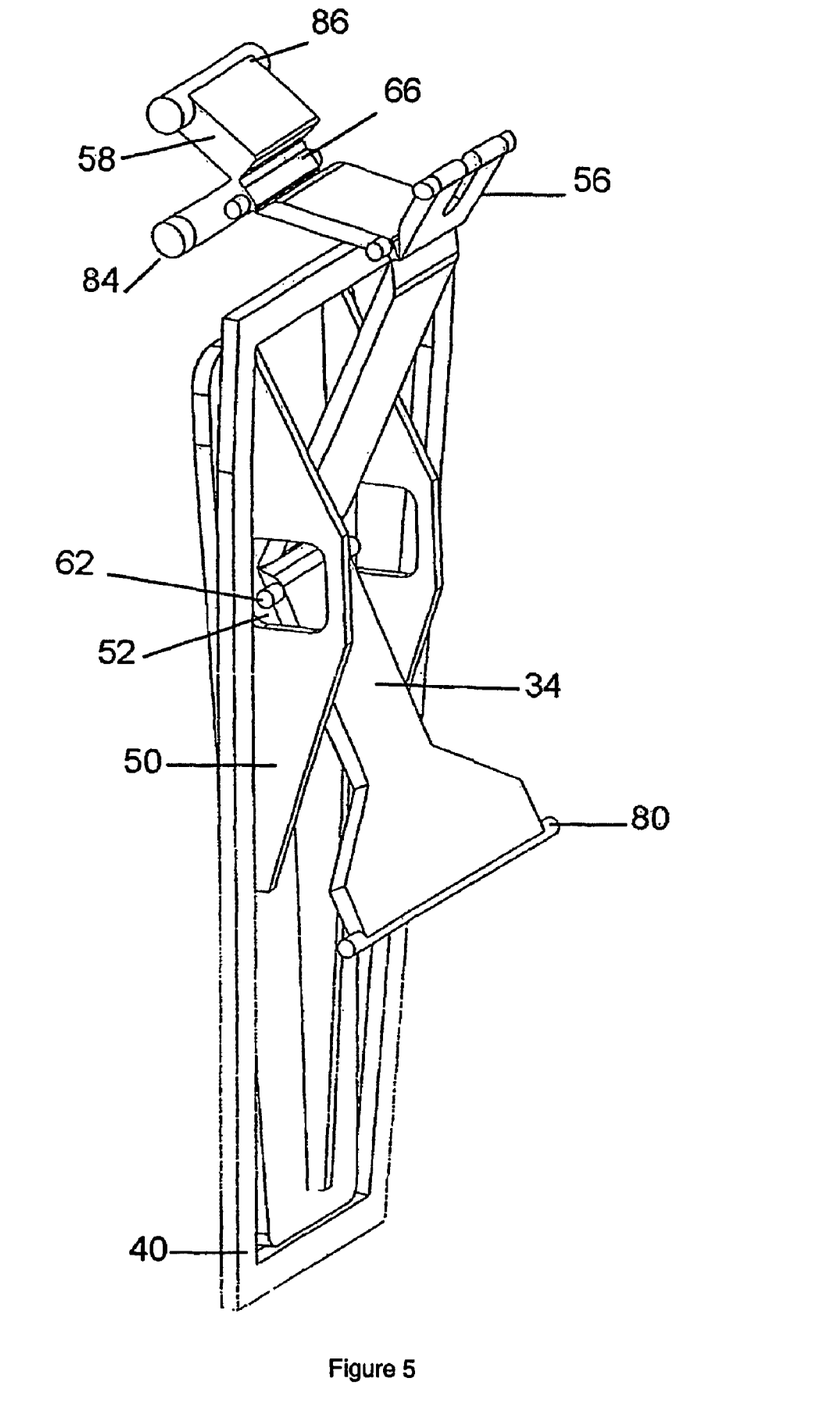
FIG. 5 shows a detailed perspective view of the pressure-responsive device and the trigger mechanism after firing of a dose.

When a patient wishes to take a dose of medication, they open cover 20 so as to access the mouthpiece 14. As the cover is opened, the cam 22 rotates, cam follower or saddle 92 moves downwards and steel bar or hook 25 is moved into engagement with the canister 23 as shown in FIG. 3. As the cam continues to rotate, the bar 25 pushes the canister into the canister carriage 24 and only then does the trigger mechanism bear much of the force of the main spring, which was previously carried by the cam. In this primed position, the patient places their mouth over the mouthpiece 14 so as to create a seal and inhales. Air is drawn in through the apertures in the air passageway wall and through the slots 11, creating a through-flow of air which produces a pressure drop of about 0.5 kPa in the device which causes the tongue of the pressure-responsive device to move. As the tongue moves in response to an intake of breath, the trigger link 54 is pulled under center as shown in FIGS. 3 and 5. An air valve could be added to the air passage to reduce the pressure drop at a given flow rate once the canister has been fired.

As the trigger link 54 moves into this under center position as shown in FIG. 5, the biasing torsion spring 70 pushes the intermediate link 56 under center. The power link 58 is pulled under center due to the interconnection of the power link and the intermediate link, and the power link moves into a substantially V-shape. The overall height or extent of the power link is thus reduced and the two main springs held on spring carriage 26 are released to expand and urge the canister against stem block and so depress a valve stem to release a dose.

This toggle-type trigger mechanism is very sensitive, with only a small pressure drop of around 0.5 kPa across the pressure-responsive device 40 being required to produce a force of around 0.5N to cause the trigger link 54 to move. Once a dose has been dispensed, the cover 20 is closed and the cover cam rotates to reset the power and trigger links into the rest position. A cantilever carried on saddle 92 pushes the trigger link over center to complete reset of the trigger mechanism.

Figure 6:
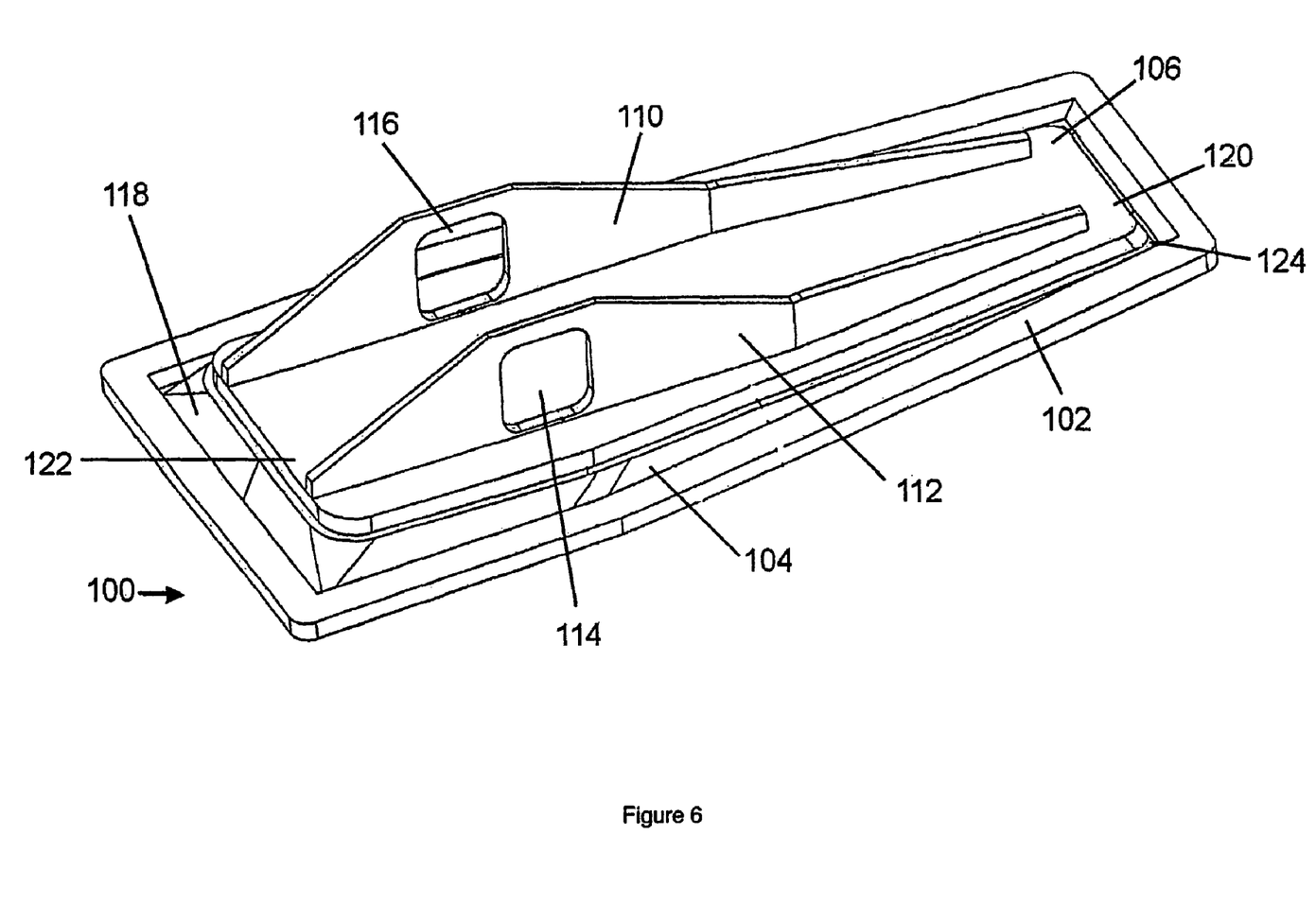
FIG. 6 shows a perspective view of the pressure-responsive device.

A detailed view of the pressure-responsive device 100 when connected to the trigger mechanism is shown in FIG. 6, the pressure-responsive device comprising a closed rectangular frame 102 made of polyethylene or high density polyethylene, a supporting membrane 104 of approximately 10 microns thick made of high density polyethylene and welded to the frame, and a tongue 106 fixed to and carried on the membrane. Integral wings 110, 112 are moulded to the tongue 106, and each wing or web has a square aperture 114, 116 for receiving pin 62 of the trigger link, as already discussed. The frame 102 is capable of snapfit connection into the internal end 37 of the air passageway 36 so as to seal the passageway at one end, or can be ultrasonically welded to the internal end 37. The membrane 104 prevents uncontrolled leaks around the tongue 106.

Typically the dimensions of the frame are around 60 mm×30 mm, with the frame having a thickness of around 5 mm. The tongue is made of plastics material such as polyethylene and is approximately 2 mm in thickness. Both the tongue, wings and the frame are made from a plastics material which ensures that they are essentially rigid, at least to small forces.

Figure 9:
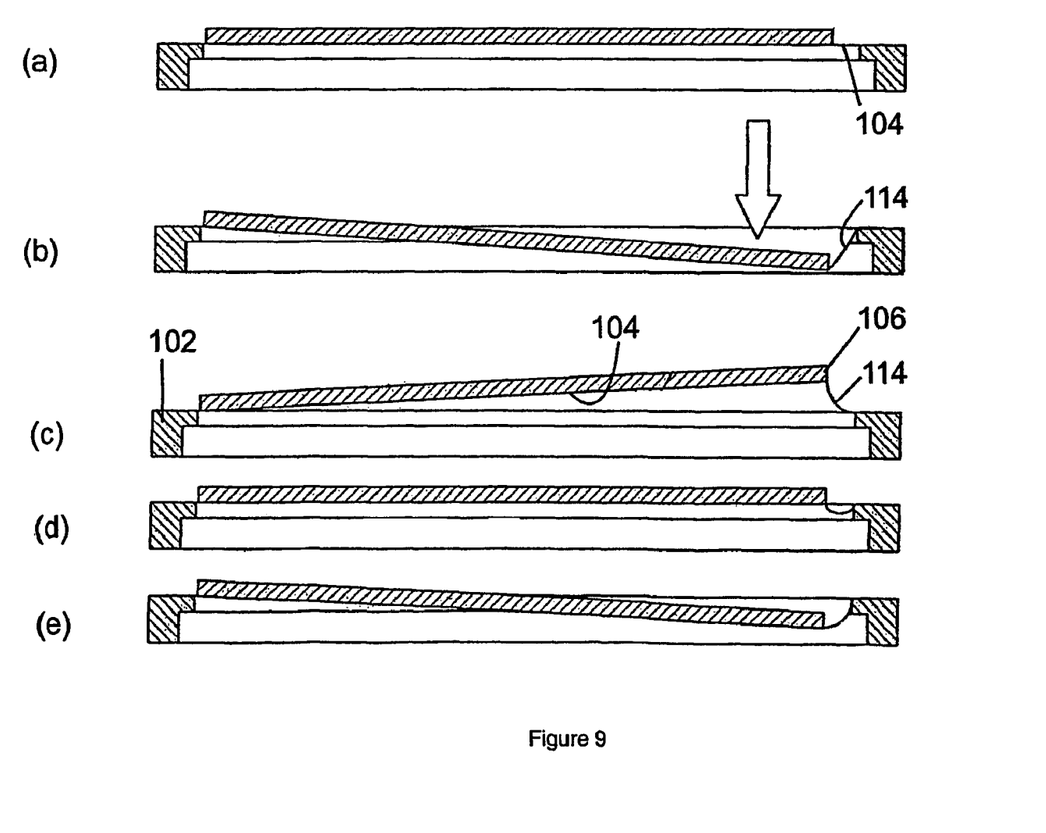
FIG. 9 is a series of views demonstrating movement of the pressure-responsive device.

The membrane is deformed in region 118, typically by a drawing process, so that a slack region is provided. Thus whilst the membrane is generally inelastic, i.e. not automatically returning to a position after deflection, the slack region provides flexibility allowing deflection of the tongue. As will be seen in FIG. 7, the tongue 106 is held within but spaced apart from the frame 102, being supported entirely by the membrane 104. The tongue 106 is tapered with a lower narrow end 120 being supported on a lower part of the membrane and an upper broad end 122 of the tongue being carried on a slack region 118 of the membrane. The slack region 118 allows movement of the upper end 122 of the tongue relative to the frame 102, with a lower part 124 of the membrane providing a hinging point about which the tongue 106 can pivot. The upper end 122 of the tongue can thus move backwards and forwards about the hinging point, as shown in FIG. 9(*c*) to (*e*), by approximately 4 mm, i.e. 8 mm total travel. The hinging point also undergoes a certain amount of movement within the frame, but to a lesser extent of around 0.5 mm backwards and forwards.

Figure 7:
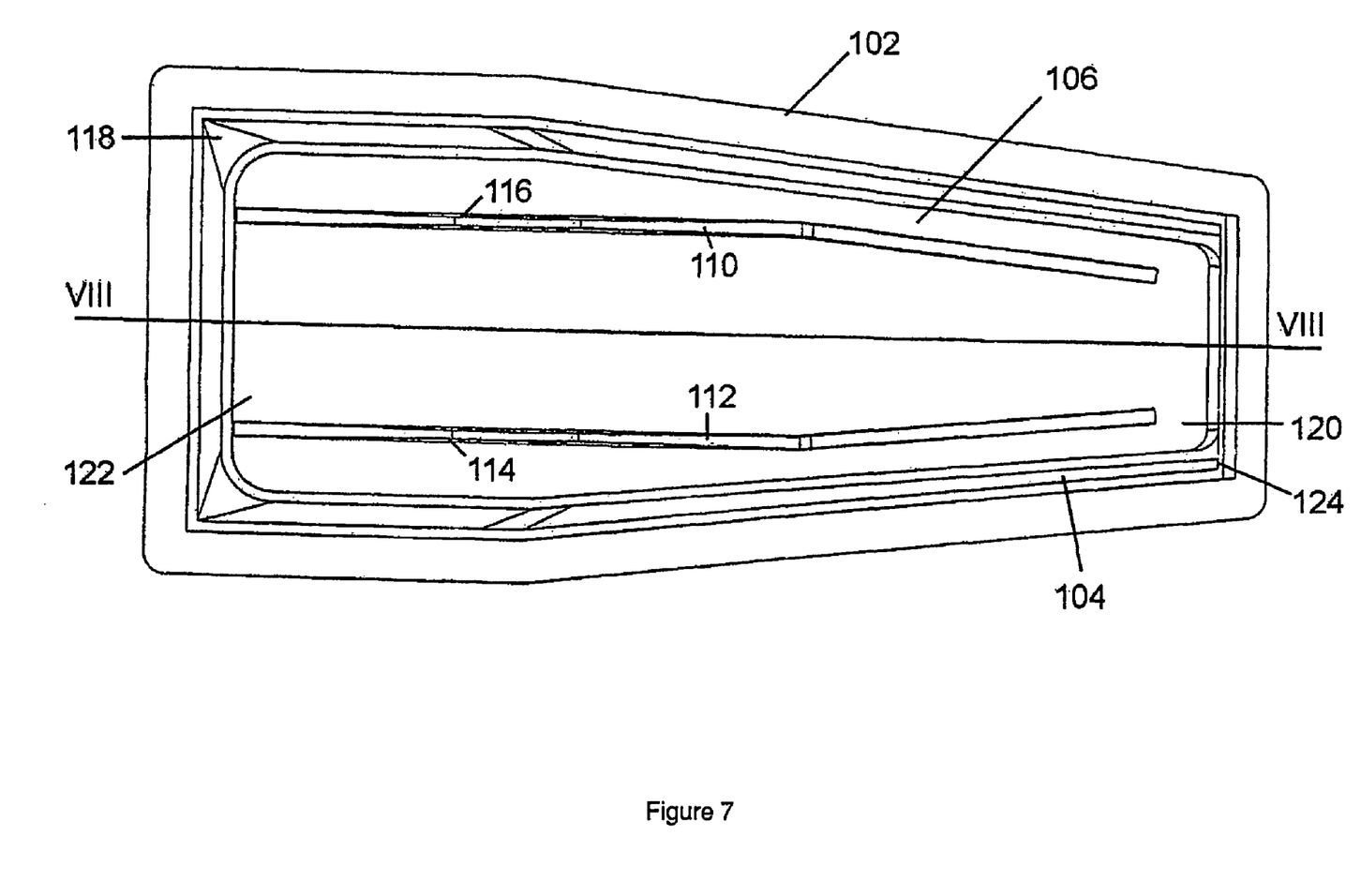
FIG. 7 shows a plan view of the pressure-responsive device.
Figure 8:
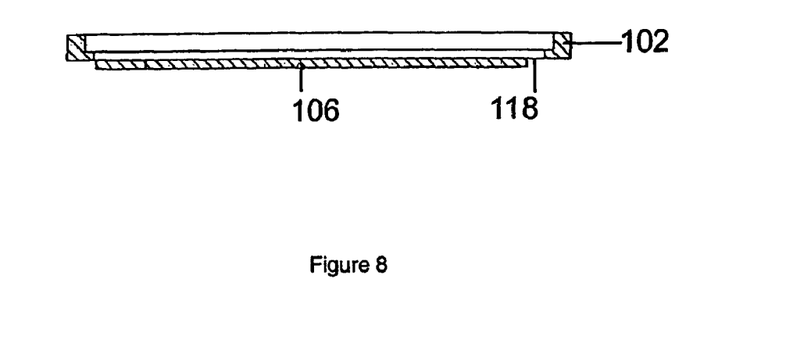
FIG. 8 shows a cross-section along line VIII-VIII of FIG. 7.

A sectional view of the pressure-responsive device along line VIII-VIII of FIG. 7 is shown in FIG. 8.

When the pressure-responsive device, or friction-free flap, is used within an inhaler, inhalation of air by a patient through the mouthpiece causes a partial vacuum which deflects the upper region 122 of tongue 106. As the tongue moves, the trigger link attached to the tongue is pulled, so releasing the trigger mechanism and dispensing a dose. By using an extremely thin web to carry the tongue, the pressure-responsive device is responsive to very low pressures and not sensitive to manufacturing tolerances as the clearance between tongue and frame is not of such small dimension as to render the pressure-responsive device inoperable if inaccuracies in manufacturing do occur.

The pressure-responsive device may be made by two rather similar methods.

Figure 10:
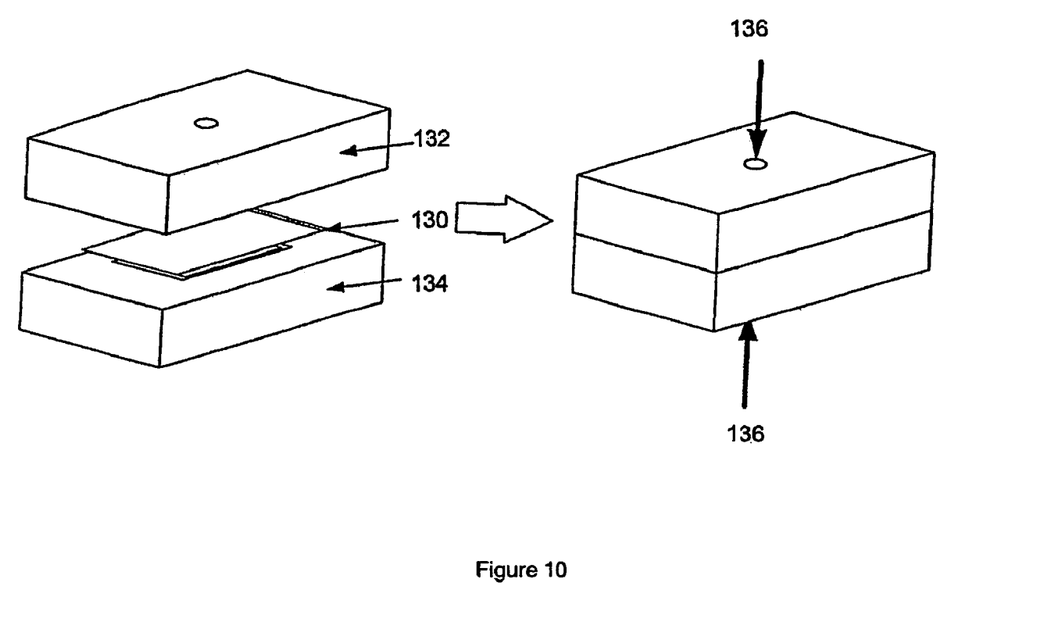
FIG. 10 is a schematic representation of a first method of moulding the pressure-responsive device.

The first method will be described with reference to FIGS. 9(*a*) and (*b*) and FIG. 10. The process used is similar to in-mould labelling, and comprises placing a film or membrane 130 of high density polyethylene of thickness 10 microns between upper and lower injection moulding tools 132, 134. The tools 132, 134 are then closed together and polyethylene injected into each tool so as to form a tongue of the pressure-responsive device within the upper tool and a frame of the pressure-responsive device within the lower tool. The frame and tongue are thus placed on either side of the membrane, and the membrane moulded whilst the tongue is within the frame so as to avoid wrinkling the membrane. If desired, the tongue and frame can be moulded on the same side of the membrane.

The materials chosen for the membrane and the frame and tongue are carefully selected so that the frame will weld to the membrane, and the membrane weld to the tongue. After moulding, see FIG. 9(*a*), the membrane is stretched at an upper region so that it yields, as seen in FIG. 9(*b*) and the tongue is then free to move back and forth as shown in FIGS. 9(*c*)-(*e*). It is important that the membrane is not an elastomer as in the post yielding process it would stretch and then recover, rather than permanently stretch. It is also important to ensure that the membrane is selected from a material that will yield without perforation as otherwise performance of the pressure-responsive device is compromised.

Figure 12:
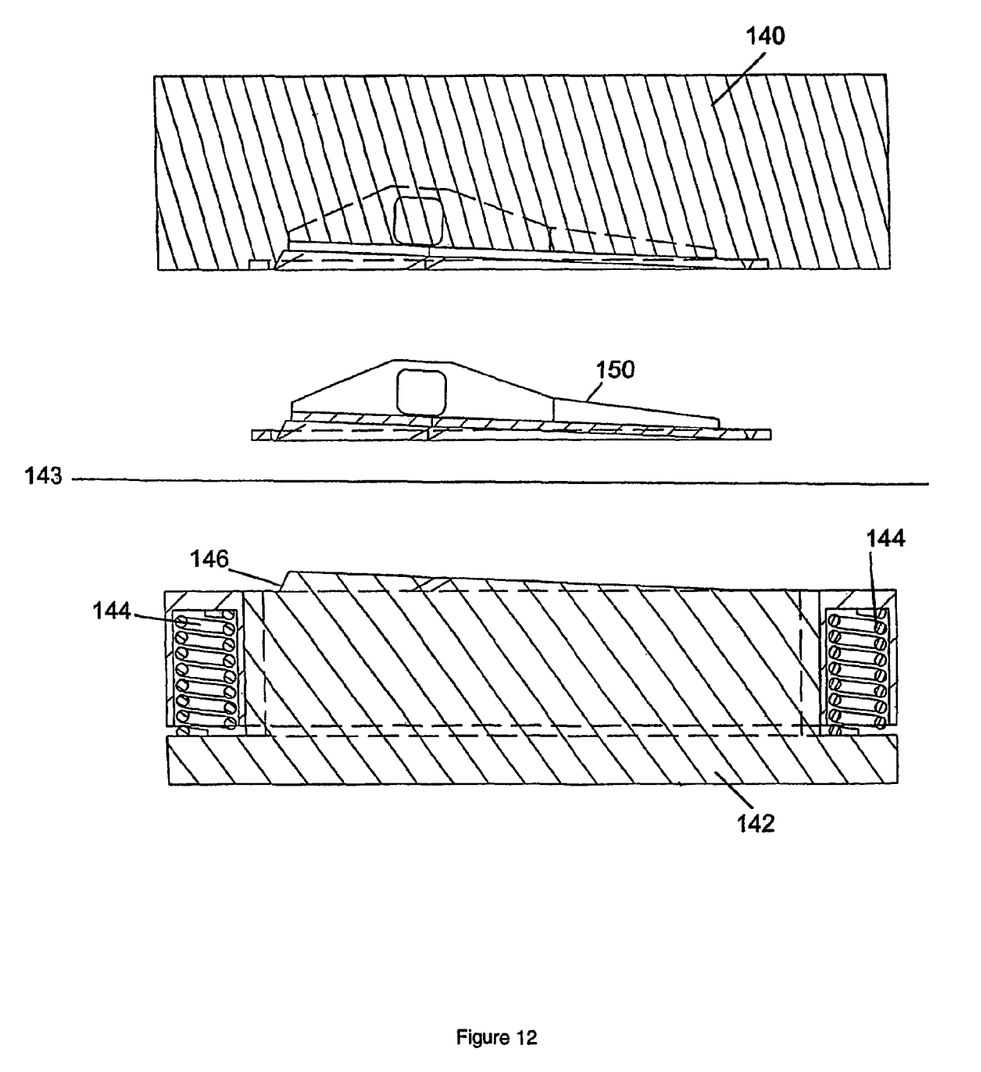
FIG. 12 is a sectional view of tooling used in a second method of moulding the pressure-responsive device.

In an alternative to purely plastic deformation of the membrane, it is possible to use a drawing process, which may be used in combination with plastic deformation. When a drawing process is used, the method is modified such that upper and lower tool faces 140, 142 are shaped such that when the membrane is clamped 143 between them, the membrane is held in position with a pressure ring 144, see FIG. 12. The tool design is such that the tongue is set at an angle to the frame, and on closing the tool, the membrane is drawn to produce the required shape. In this shape, the tongue is positioned at an angle to the frame which is greater than, or equal to, the maximum deflection which the tongue will experience in operation of the device. When the two parts 140, 142 of the tool are urged together, the membrane deforms over inclined region 146 of the tool face.

Figure 11:
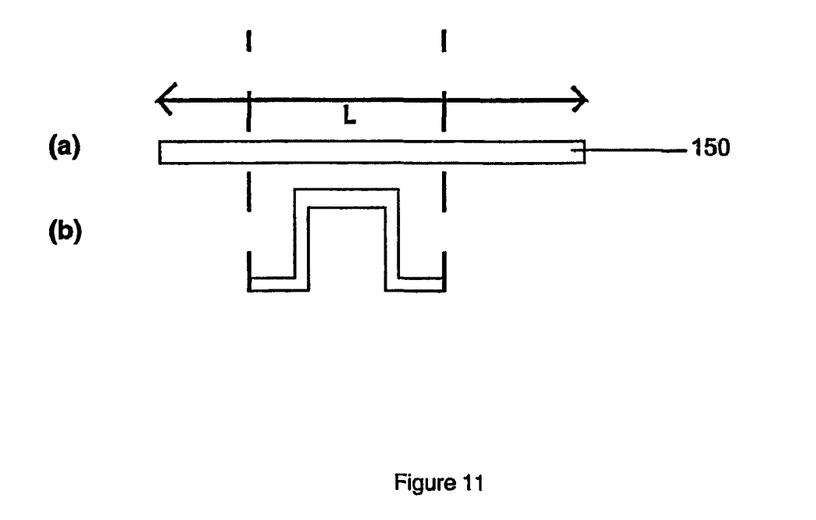
FIG. 11 is a schematic view of a drawing process used in the second method.

By using a continuous sheet of membrane and pulling material in from outside the tool, thinning of the membrane can be avoided so reducing the risk of perforation. Membranes such as EBA and EMA films which are slightly elastomeric are used. This drawing process alters the shape of the membrane without altering the thickness, see FIG. 11 where an undrawn membrane 150 of length L is shown in FIG. 11(*a*)

and a drawn membrane, of same total length but modified shape, is shown in FIG. 11(b). This provides a less concentrated stretch, where the local strain is lower and perforation is less likely than by just using plastic deformation as in the first method described.

The invention claimed is:

1. A pressure-responsive device comprising a support bearing a membrane which carries a tongue moveable in response to changes in pressure, wherein the membrane includes a slack region which allows an upper part of the tongue to move more in response to pressure than the remainder of the tongue, the remainder of the membrane acts as a hinge about which the upper part of the tongue pivots, said membrane surrounds a substantial portion of a periphery of said tongue and extends from said tongue to said support, and wherein the tongue further comprises two wings attached to one face of the tongue, the two wings each having an aperture for receiving part of a trigger mechanism.

2. A pressure-responsive device comprising:
   a support bearing a membrane which carries a tongue moveable in response to changes in pressure, wherein the membrane includes a slack region which allows an upper part of the tongue to move more in response to pressure than the remainder of the tongue and the remainder of the membrane acts as a hinge about which the upper part of the tongue pivots;
   wherein the support is a closed frame with an entire peripheral edge of the membrane fixed to the frame;
   wherein the tongue sits on the membrane within the frame, and there is a clearance region around the tongue such that the tongue and frame are separated; and
   wherein the tongue further comprises two wings attached to one face of the tongue, the two wings each having an aperture for receiving part of a trigger mechanism.

3. A method of making a pressure-responsive device comprising placing a sheet of material between upper and lower injection moulding tools, closing the tools together, injection moulding a support and a tongue within the tools and providing a slack region in the sheet between the support and the tongue, so as to allow an upper part of the tongue, to move more in response to pressure than the remainder of the tongue, the remainder of the sheet acting as a hinge about which the upper part of the tongue pivots.

4. A method according to claim 3, wherein the support and the tongue are either formed on the same side of the sheet, or on opposite sides.

5. A method according to claim 4, wherein the method further comprises distorting the sheet by stretching to achieve plastic deformation of a region of the sheet, so as to provide the slack region.

6. A method according to claim 5, wherein the method further comprises drawing part of the sheet into the tool as forming occurs, thereby to limit the amount of stretch undergone by the sheet.

7. A method according to claim 4 wherein the method further comprises drawing part of the sheet into the tool as forming occurs, thereby to limit the amount of stretch undergone by the sheet.

8. A pressure-responsive device comprising a support bearing a membrane which carries a tongue moveable in response to changes in pressure, wherein the membrane includes a slack region which allows an upper part of the tongue to move more in response to pressure than the remainder of the tongue, the remainder of the membrane acts as a hinge about which the upper part of the tongue pivots, and wherein the tongue is tapered along its length, having an upper broad region and a lower narrow region, with the upper broad region being carried by the slack region of the membrane.

* * * * *